United States Patent [19]

Neumann

[11] Patent Number: 5,682,146

[45] Date of Patent: Oct. 28, 1997

[54] METHOD OF MONITORING AN ADVANCING YARN

[75] Inventor: Bernd Neumann, Radevormwald, Germany

[73] Assignee: Barmag AG, Remscheid, Germany

[21] Appl. No.: 362,425

[22] PCT Filed: Apr. 26, 1994

[86] PCT No.: PCT/EP94/01317

§ 371 Date: Mar. 20, 1995

§ 102(e) Date: Mar. 20, 1995

[87] PCT Pub. No.: WO94/25870

PCT Pub. Date: Nov. 10, 1994

[30] Foreign Application Priority Data

Apr. 29, 1994 [DE] Germany .................. 43 14 049.1

[51] Int. Cl.⁶ ................................................ G08B 21/00
[52] U.S. Cl. .............. 340/677; 340/825.23; 364/470; 57/264; 57/58.84
[58] Field of Search ............... 340/677, 825.23; 57/264, 58.84; 364/470, 563

[56] References Cited

U.S. PATENT DOCUMENTS

| | | |
|---|---|---|
| 3,731,069 | 5/1973 | Goto et al. |
| 4,256,247 | 3/1981 | Loepfe ................. 340/677 |
| 4,306,231 | 12/1981 | Bagnall ................. 340/677 |
| 4,415,008 | 11/1983 | Keller ................... 340/677 |
| 4,476,901 | 10/1984 | Sainew ................. 340/677 |
| 4,656,465 | 4/1987 | Erni ..................... 340/677 |
| 4,720,702 | 1/1988 | Martens ................ 340/677 |
| 4,774,673 | 9/1988 | Aemmer ............... 340/677 |
| 4,951,030 | 8/1990 | Jones ................... 340/677 |
| 5,017,911 | 5/1991 | Muller .................. 340/677 |
| 5,018,390 | 5/1991 | Muller . |
| 5,055,829 | 10/1991 | Stuttem ................ 340/677 |
| 5,164,710 | 11/1992 | Anderegg ............. 340/677 |

Primary Examiner—Jeffrey Hofsass
Assistant Examiner—Albert K. Wong
Attorney, Agent, or Firm—Bell, Seltzer, Park & Gibson, P.A.

[57] ABSTRACT

Method of monitoring the quality of an advancing yarn by continuously measuring the yarn tension, which includes determining the progression of the yarn tension upon occurrence of a defined failure (failure record), storing the failure record in a data memory, comparing the measured yarn tension with the failure record and generating an alarm signal, when a range of the yarn tension progression shows a similarity to the failure record.

7 Claims, 2 Drawing Sheets

METHOD OF MONITORING AN
ADVANCING YARN

BACKGROUND OF THE INVENTION

The present invention relates to a method of monitoring the quality of an advancing yarn during the production or processing of the yarn.

U.S. Pat. No. 4,720,702 discloses a method of monitoring the yarn tension at each of a plurality of yarn texturing stations, while continuously determining the mean value of the monitored tension at each station and while also continuously determining the differential between the monitored value and the mean value. Also, an alarm signal is generated whenever the mean value, or the differential value, leaves a predetermined tolerance range.

The significance of the known method lies in that, in a texturing process, the yarn tension is continuously determined, and that by evaluating the yarn tension, however, it is not the progression of the process that is determined, but the quality of the yarn processed by the texturing method. This is based on the experience that the yarn tension, which is measured in the texturing process downstream of the false twist friction unit, allows with a certain evaluation of the yarn tension to draw conclusions as to the quality of the produced yarn, without defining, determining and gathering those process parameters, which are causal for the quality or absence of quality.

It is therefore the object of this invention to determine by evaluation of the yarn tension which is continuously measured in the course of the production and/or processing of a yarn, the causes of non-conformities, which affect the quality of the yarn.

SUMMARY OF THE INVENTION

The above and other objects and advantages of the present invention are achieved by the provision of a method of monitoring the quality of an advancing yarn which comprises the steps of determining a characteristic progression of the yarn tension resulting from at least one non-conformity in the quality of the yarn, storing at least significant features of the determined progression as a non-conformity record in a data memory, then continuously monitoring the tension of the advancing yarn while continuously comparing the measured yarn tension with the non-conformity record, and generating a signal whenever a progression of the measured yarn tension shows a similarity to the stored non-conformity record, so as to indicate the occurrence of a quality non-conformity and permit the identification thereof.

According to the present invention, a portion of the graphic record of the yarn tension, the progression of which is symptomatic of certain, defined non-conformities, is stored as a pattern for this non-conformity (failure record), and subsequently compared with the progression of the yarn tension. The term non-conformity is understood to mean a certain defect, trouble, error, fault or failure of the yarn tension which is different from a conformity state, i.e. a normal one. In this comparison, it is recognized that the progression of the yarn tension in the course of time does not recur identically, when a certain non-conformity occurs, but only with certain characteristics. In one embodiment of this invention, the failure records are therefore not stored as a defined function, but in a typified form, a possible scattering of the progression of the yarn tension in the course of time being taken into account. This means that the characteristic progression of the yarn tension is stored, when a certain non-conformity occurs, but with such a lack of definition or tolerance (non-conformity pattern) that the non-conformity pattern is still indicative of the non-conformity with an adequate certainty, whereas, on the other hand, it still covers as many forms of the non-conformity record as possible in the case of the non-conformity concerned.

In a second embodiment of the invention, the non-conformity record may be stored in form of the directly measured record. In this instance, criteria of similarity which have formed the basis for the comparison between the non-conformity record and yarn tension record, are input in the computer separately (comparison logic), and superimposed in the evaluation of the comparison. The similarity is defined by a correlation coefficient indicating the percentage of measuring values which are within the non-conformity mask. What turns out to be a non-conformity is determined by the operator of the system for producing or processing the advancing yarn. Included may be all process parameters of the process and all properties of the yarn, to the extent that these parameters or properties are causal for adequately characteristic progressions of the yarn tension.

Occasionally, a non-conformity in the process or the yarn may show only in the finished product, for example, in the woven or knit fabric as an unevenness, different dye absorption, waviness, or the like. For such non-conformities, entire complexes of causes are causal, without it being possible to define the individual causes. However, even in these instances, it is possible to observe, whether such negative effects on the finished product have been indicative already before in the production or processing of the yarn as a result of a characteristic progression of the yarn tension. Thus, the record of the actual yarn tension is compared in the computer with the non-conformity record, via the comparison logic, or with the non-conformity pattern or several non-conformity patterns or with significant characteristic parameters derived therefrom, and in the event of consistency, a signal is emitted which indicates the occurrence of the non-conformity. In addition, however, it is possible, for purposes of identifying the non-conformity, to perform further evaluations of the yarn tension record, for example, upon occurrence of extreme values, considerable fluctuations in the course of time and in a short succession, average value, and exceeding certain tolerance values for the average value scanning the measured yarn tension for significant parameters derived from the non-conformity record, or the like. It is also possible to output a probability signal indicative of a certain non-conformity such as: x% of the measuring values are within the non-conformity record or y% probability for the non-conformity of "missing preparation" or (100—y%) of filament break. To output a probability signal is possible because in the majority of cases the progression of yarn tension is within a range of fluctuation for which a probability signal can be determined.

The result of the comparison is a quality signal. This quality signal may be used for influencing the method of producing or processing the yarn. Prerequisite in this instance is that an "online" evaluation occurs, i.e., the comparison between the yarn tension record and the non-conformity record or non-conformity pattern or non-conformity mask occurs directly, when a measured value is output.

However, it is also possible to use the quality signal for identifying the quality of the wound yarn package. In this instance, the "online" method is possible. However, it is also possible to store the yarn tension record, or at least a large portion thereof, and to subsequently conduct the comparison ("offline").

This "offline" method may likewise be utilized, so as to subsequently correct the process parameters for the further production, and to monitor the process.

BRIEF DESCRIPTION OF THE DRAWINGS

Some of the objects and advantages of the present invention having been stated, others will appear as the description proceeds, when considered in conjunction with the accompanying drawings, in which.

DETAILED DESCRIPTION OF THE PREFERRED EMBODIMENT

Figure 1:
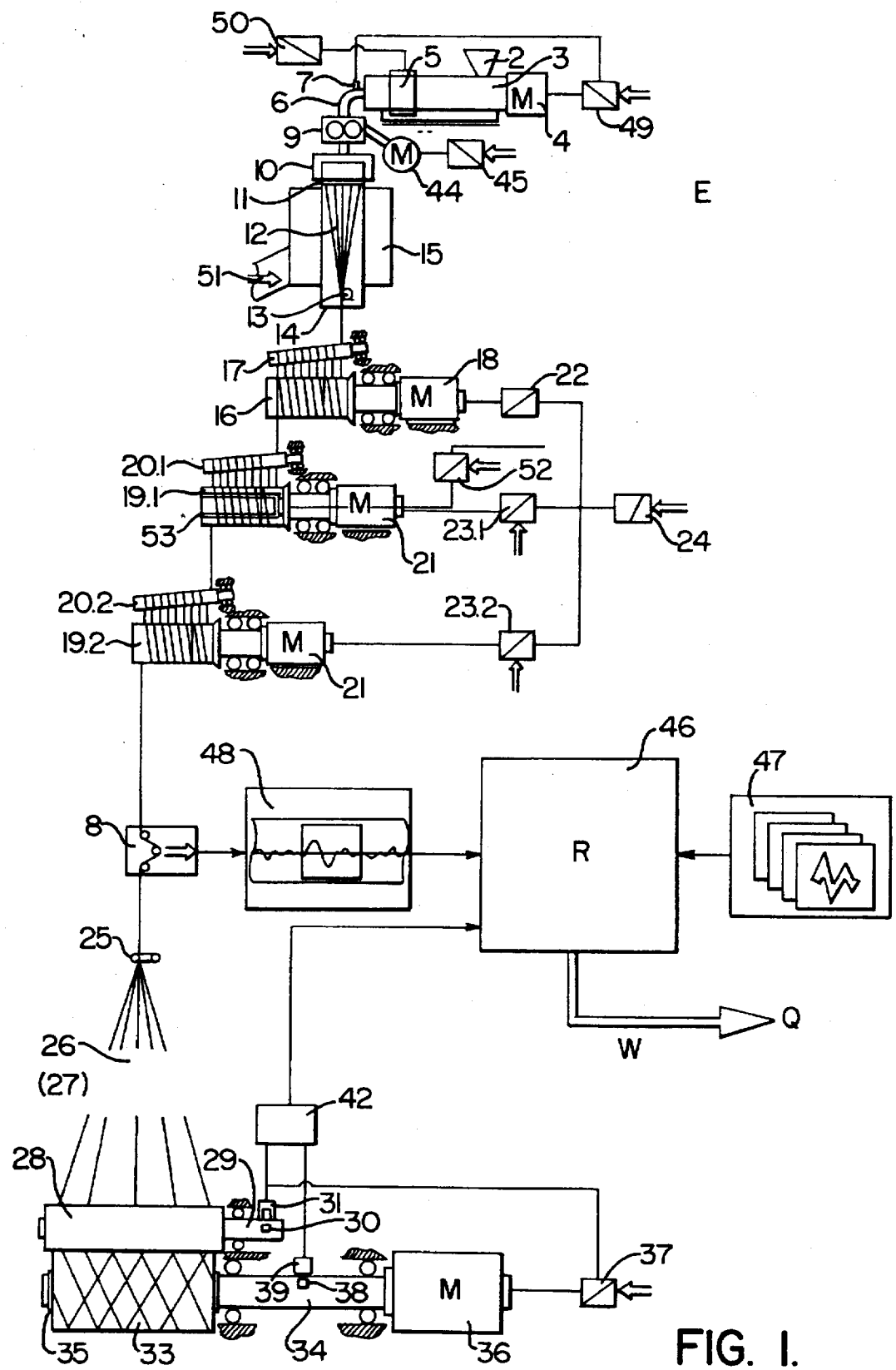
FIG. 1 is a schematic view of a yarn spinning process which embodies the features of the present invention.

A yarn 1 is spun from a thermoplastic material. The thermoplastic material is supplied through a feed hopper 2 to an extruder 3. The extruder 3 is driven by a motor 4, which is controlled by a motor control 8. In the extruder, the thermoplastic material is melted. To this end, the deformation work is utilized which is introduced into the material by the extruder. In addition, a heating system 5 in the form of a resistance heater is provided, which is controlled by a heating control 50. Through a melt line, the melt enters into a gear pump 9, which is driven by a pump motor 44. The latter is controlled by a pump control 45 such as to permit a very fine adjustment of the pump speed. Pump 9 delivers the melt flow to a heated spin box 10, the underside of which accommodates a spinneret 11. From spinneret 11, the melt emerges in the form of fine filament sheets 12. The latter advance through a cooling or quench chamber 14, in which an air current is directed by blowing 15 transversely or radially to the sheet of filaments, thereby cooling the filaments.

At the outlet end of cooling chamber 14, the sheet of filaments is combined by a spin finish application roll 13 to a yarn 1 and provided with a fluid spin finish. Thereafter, the yarn is withdrawn from the cooling chamber and the spinneret by a delivery roll or godet 16. The yarn loops several times about the godet. To this end a guide roll 17 is used which is arranged in crossed relationship with respect to godet 16. Guide roll 17 is freely rotatable. Godet 16 is driven by a motor 18 and a frequency converter 22 at a preadjustable speed. This withdrawal speed is by a multiple higher than the natural exit speed of the filaments from spinneret 11.

Arranged downstream of godet 16 is a pair of draw rolls or godets 19.1 and 19.2 with further guide rolls 20.1 and 20.2. Both correspond in their arrangement to godet 16 with guide roll 17. For the drive of draw rolls 19.1 and 19.2, motors 21.1 and 21.2 with frequency converters 23.1 and 23.2 are used. The input frequency of frequency converters 22, 23.1 and 23.2 is evenly predetermined by a controllable frequency generator 24. In this manner, it is possible to individually adjust on frequency converters 22, 23.1 and 23.2 the speed of godet 16 and draw rolls 19.1 and 19.2, whereas the speed level of godet 16 and draw rolls 19.1 and 19.2 is collectively adjusted on frequency generator 24.

From the last draw roll 19.2, yarn 1 advances to a so-called "apex yarn guide" 25, and thence to a traversing triangle 26. Not shown in FIG. 1 is a yarn traversing mechanism, which may be a cross-spiralled roll with a yarn guide traversing therein and reciprocating the yarn over the length of a package 33. Following yarn traversing mechanism 27, the yarn loops about a contact roll 28. The latter rests against the surface of package 33, and serves to measure the surface speed of package 33. Package 33 is formed on a tube 35, which is slipped onto a winding spindle 34. Winding spindle 34 is driven by a spindle motor 36 and a spindle control 37 such that the surface speed of package 33 remains constant. To this end, the speed of freely rotatable contact roll 28 is sensed as a control variable on its shaft 29 by means of a ferromagnetic insert 30 and a magnetic pulse generator 31.

The first draw roll 19.1 possesses a heating system 53, which allows to heat the godet jacket and the yarn accordingly, thereby influencing to a great extent the yarn properties which are realized by the drawing. The temperature of heating system 53 is controllable by a heating control 52.

Arranged downstream of the second draw roll 19.2 and in the path of the or is a yarn tension sensor=yarn tensiometer 8, which generates a signal representing the yarn tension. In a device 48, the continuously measured yarn tension is output as a graphic record of the yarn tensile force (yarn tension record). The output signal of device 48 is input in a computer unit 46. The latter allows to store the yarn tension record for the entire winding cycle or for essential—selected—portions of the winding cycle.

On the other hand, the computer is connected with a non-conformity record memory 47. Stored in the non-conformity record memory are so-called "non-conformity records" or "non-conformity patterns." Within the scope of the present invention, the characteristic progression of the yarn tension is stored, which has previously been determined by tests to be symptomatic of a certain non-conformity. In addition or alternatively, it is also possible to determine and store the characteristic progression of a variable, which is derived from the yarn tension. Considered as such variables are, for example, the first or second derivative of the progression of the yarn tension, the standard deviation of the yarn tension, the average value, the deviation of the yarn tension from predetermined limit values, and others. Essential is to determine for each form of non-conformity, which of these variables, i.e., yarn tension or a variable derived therefrom has a characteristic that is especially representative of the non-conformity.

Consequently, the measured yarn tension is converted in device 48 to a derived variable, even when the non-conformity record is stored as a derived variable.

When storing this non-conformity record, it will be necessary to additionally store the criteria of similarity in a memory 47. The memory 47 is a logic module, which allows to predetermine the limit ranges for the comparison of the numerically input values of the yarn tension record, on the one hand, and of the non-conformity record on the other.

Thus, the computer allows to emit a positive signal not only in the event of a numerical consistency, but also when a consistency is found in certain limit ranges.

Alternatively however, it is also possible to output the non-conformity record already in memory 47 as a so-called "non-conformity pattern." Within the scope of the present invention, a non-conformity pattern is described as the non-conformity record, when it is prepared such that all possible progressions of the yarn tension are determined and stored, which characteristically appear at a certain non-conformity. In this instance, the comparison proceeds in computer 46 in the meaning that it is examined, whether the actual yarn tension record (or the variable derived therefrom) falls under the stored ranges of the non-conformity pattern.

Figure 2:
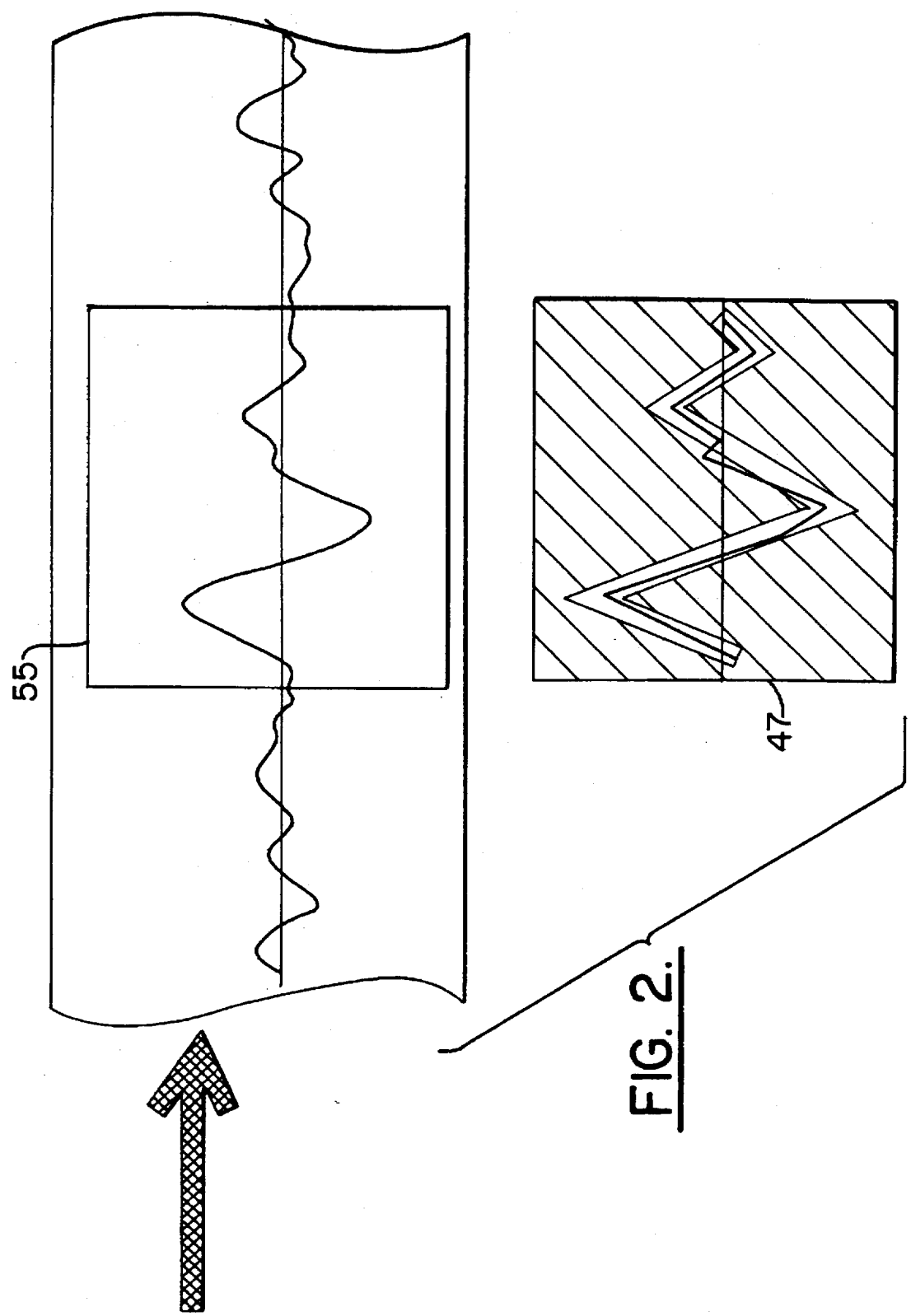
FIG. 2 is a graphic record of the monitored yarn tension and a non-conformity mask.

Indicated in FIG. 1 and—even more clearly—in FIG. 2 by a rectangle 55 is a range in the yarn tension record, in which a certain non-conformity occurs. Typically, it will be a fluff, for example, entanglement of a filament, which results from the break of a filament. The passage of such an entanglement through the yarn tension sensor 8 leads to a very sudden, steep increase of the yarn tension, and subsequently to a fluctuation about the average value. The slope of the increase, the extreme values, as well as the fluctuation frequency are dependent on the intensity of the entanglement and the thereby caused discontinuity in the exterior of the yarn. Characteristic, however, is the fluctuation of the yarn tension which is initially triggered and initiated by a very steep increase of the yarn tension. In memory 47, this progression is stored such that a wide range of amplitudes and frequencies of the fluctuation is covered. This range is laid out to such an extent as to allow in any event to still obtain a reliable indication that a knotlike entanglement has passed through the yarn tension sensor.

In the illustrated embodiment, the computer 46 generates a quality signal Q.

The quality signals Q, which, as aforesaid, have been generated, are further processed as follows: the quality signal may be emitted as an optical or acoustical alarm, or as a graphic record. The graphic record is used to mark and classify the produced yarn package.

Alternatively or additionally, the quality signal may be supplied thereafter, in particular to one or more of the control devices 22 for draw roll 16; and/or 23.1, 23.2 for the second draw rolls 19.1 and/or 19.2 so as to influence the draw ratio;

24 for controlling the withdrawal speed;

45 for controlling the pump speed;

49 for controlling the extruder speed;

50 for controlling the heating system;

51 for controlling the cooling device; and 37 for controlling the takeup speed.

The extruder control is activated, in particular when a metering pump 9 is absent. In this instance, the extruder will act as a pump, and the activation of the extruder control, i.e., the rotational speed of the extruder will allow to influence the output of the extruder.

The use of a metering pump 9 permits to influence the quantity which is put through spin head 10 and spinneret 11, in that pump control 45 is activated, thus controlling the rotational speed of pump 9.

The activation of cooling air control 51 allows to influence the cooling. This becomes effective on the denier of the yarn. In particular, it is also possible to influence the evenness of the individual filaments with the use of special cooling devices which allow to cool the sheets of filaments and/or the spinneret in sections.

In the embodiment of FIG. 1, individual elements of the system are exchangeable, if possible. Accordingly, different parameters are controlled in this instance. In particular, it is possible to replace the extruder with a discharge pump, and likewise there exist various other possibilities of cooling the sheet of filaments. Likewise, an additional heating may be used in, or in the place of, the draw elements.

The current high-speed spinning processes even allow to omit the drawing by the godets. In this instance, the yarn is either withdrawn by a single godet from the spinneret and advanced to the winding head, or it is directly withdrawn from the spinneret by the takeup device. On the other hand, it is also possible to replace or supplement the drawing by further elements, such as for example, an additional heating system, in particular a tubular heater.

The illustrated embodiment permits to use the quality parameter Q for activating withdrawal control 24 and/or draw roll control 23.1 and/or 23.2.

The activation of delivery control 24 allows to influence the speed of godet 16 and godets 19.1 and 19.2, without changing the speed ratio. In this instance, the draw ratio remains constant, while the yarn speed is varied. This allows to influence the denier of the yarn.

The activation of draw roll control 23.1 or 23.2 allows to influence the speed ratio between godets 19.1/19.2/16, and thus the draw ratio. The change in the draw ratio makes it possible to vary both the physical properties and the denier of the yarn.

Finally, the spindle control permits to also vary, by means of the quality parameter, the circumferential speed of yarn package 33, which is controlled by contact roll 28. This allows to influence in particular the package buildup and the tension, under which the yarn is deposited on the package.

On the other hand, the method of the present invention allows to determine all of the above-described influential parameters, when it has previously been found by tests that non-conformities with respect to these influential parameters result in a characteristic progression of the yarn tension. Thus, it is possible to detect in particular:

a change in the denier by adjusting the pump speed 44, heating 5, by contamination of the spinneret, by varying the withdrawal speed of godet 16;

an absence of filaments, for example, as a result of filament breakage;

an absence of spin finish (consumption of spin finish fluid, breakdown of spin finish application roll 13);

a variation of the draw ratio, for example, by contamination or abrasion of godets 16, 19.1, 19.2;

a change in physical properties, for example, by guideways of heater 53; and a variation of the takeup speed, for example, by an irregular operation of contact roll 28.

The fact that logic module 47 or the input of a non-conformity pattern mask is not used to conduct a numerical comparison, but is used for a comparison of ranges of the yarn tension, will limit the reliability of indication with respect to the non-conformity to be found, i.e., it may happen that the indication determined by computer 46 is not clear. In such an instance, it is possible to also include further parameters or variables derived therefrom, so as to make the non-conformity indication of the quality signal more specific. As shown in FIG. 1, the comparison between the spindle speed and the speed of contact roll 28 results in that computer module 42 generates a signal, which represents the package diameter or a variable derived therefrom, for example, the increase of the package per unit time. This output signal is additionally input in computer 46 and also used to evaluate the yarn tension record. Thus, on the one hand, the comparison of the yarn tension record with the non-conformity pattern, which symbolizes a knotlike entanglement, allows to diagnose such an entanglement and to simultaneously verify that the increase of the package changes at the same time, when this characteristic progression of the yarn tension occurs.

Such a change in the increase of the package points likewise to the fact that not all filaments, of which the yarn consists, advance free of trouble and continuously.

I claim:

1. A method of monitoring the quality of an advancing yarn comprising the steps of determining a characteristic progression of the yarn tension resulting from at least one non-conformity in the quality of the yarn, storing at least significant features of the determined progression as a non-conformity record in a data memory, then continuously monitoring the tension of the advancing yarn, while continuously comparing the monitored yarn tension with the non-conformity record, and generating a signal whenever a progression of the monitored yarn tension shows a similarity to the stored non-conformity record, so as to indicate the occurrence of a quality non-conformity and permit the identification thereof, the step of determining a characteristic progression of the yarn tension including generating a non-conformity mask of the non-conformity record, and the step of comparing the monitored yarn tension with the non-conformity record including superimposing the mask and the monitored yarn tension.

2. The method as defined in claim 1 wherein the step of determining a characteristic progression of the yarn tension includes determining a variable which is derived from the yarn tension, and wherein the step of comparing the measured yarn tension with the non-conforming record includes determining the corresponding variable which is derived from the monitored yarn tension and comparing the two determined variables.

3. The method as defined in claim 1 wherein the step of comparing the monitored yarn tension with the non-conformity record further includes determining a correlation coefficient which indicates the percentage of the monitored yarn signal which appears within the non-conformity mask.

4. The method as defined in claim 3 wherein the step of generating a signal includes generating a signal which is selected from the group consisting of (a) x% of the monitored yarn tension which is within the mask;

(b) y% probability of a predetermined non-conformity; and (c) (100—y%) of filament break.

5. A method for producing a synthetic filament yarn comprising the steps of extruding a plurality of filaments through a spinneret and while advancing the filaments downwardly through a cooling shaft positioned below the spinneret, collecting the downwardly advancing filaments to form an advancing yarn, drawing the advancing yarn, and winding the resulting drawn yarn into a yarn package, and characterized by the further step of monitoring the quality of the advancing yarn and which comprises the steps of (a) determining a characteristic progression of the yarn tension resulting from at least one non-conformity in the quality of the yarn, (b) storing at least significant features of the determined progression as a non-conformity record in a data memory, then (c) continuously monitoring the tension of the advancing yarn, while (d) continuously comparing the monitored yarn tension with the non-conformity record, and (e) generating a signal whenever a progression of the monitored yarn tension shows a similarity to the stored non-conformity record, so as to indicate the occurrence of a quality non-conformity and permit the identification thereof, the step of determining a characteristic progression of the yarn tension including generating a non-conformity mask of the non-conformity record, and the step of comparing the monitored yarn tension with the non-conformity record including superimposing the mask and the monitored yarn tension.

6. The method as defined in claim 5 comprising the further step of utilizing the generated signal to modify at least one operating parameter of the method so as to have a corrective influence on the identified quality non-conformity.

7. The method as defined in claim 5 wherein the step of continuously monitoring the tension is conducted at a location downstream of the drawing step and before the winding step.

* * * * *